US006963402B2

(12) United States Patent
Chism, II (10) Patent No.: US 6,963,402 B2
(45) Date of Patent: Nov. 8, 2005

(54) POLARIZATION MODULATION PHOTOREFLECTANCE CHARACTERIZATION OF SEMICONDUCTOR QUANTUM CONFINED STRUCTURES

(76) Inventor: William W. Chism, II, 2100 Newfield La., Austin, TX (US) 78703

( * ) Notice: Subject to any disclaimer, the term of this patent is extended or adjusted under 35 U.S.C. 154(b) by 0 days.

(21) Appl. No.: 10/847,202

(22) Filed: May 17, 2004

(65) Prior Publication Data

US 2004/0257566 A1 Dec. 23, 2004

Related U.S. Application Data

(60) Provisional application No. 60/472,687, filed on May 22, 2003.

(51) Int. Cl.$^7$ ............................. G01J 4/00; G01N 21/55
(52) U.S. Cl. ........................ 356/369; 356/447; 250/225
(58) Field of Search ........................... 356/237.1–237.5, 356/364–369, 445–448; 250/225, 559.22, 559, 49

(56) References Cited

U.S. PATENT DOCUMENTS

| | | | | |
|---|---|---|---|---|
| 3,982,207 | A | | 9/1976 | Dingle et al. |
| 4,750,822 | A | * | 6/1988 | Rosencwaig et al. ....... 356/445 |
| 4,931,132 | A | | 6/1990 | Aspnes et al. |
| 5,501,637 | A | * | 3/1996 | Duncan et al. ............. 374/126 |
| 5,536,936 | A | * | 7/1996 | Drevillon et al. .......... 250/226 |
| 5,757,671 | A | * | 5/1998 | Drevillon et al. .......... 356/367 |
| 6,195,166 | B1 | | 2/2001 | Gray et al. |
| 6,400,449 | B2 | * | 6/2002 | Maris et al. .................. 356/72 |

OTHER PUBLICATIONS

Airaksinen et al, "Photoreflectance study of photovoltage effects in GaAs diode structures," Appl. Phys. Lett., 60:17, 2110–2112, Apr. 27, 1992.

Aspnes, "Characterization of semiconductors and semiconductor structures by optical techniques/optical properties of materials and structures," SPIE, Oct. 1990.

Aspnes, "Observation and analysis of epitaxial growth with reflectance–difference spectroscopy," Materials Science and Engineering B30, 109–119, 1995.

Glembocki et al., "Photoreflectance characterizatiion of interband transitions in GaAs/AlGaAs multiple quantum wells and modulation–doped heterojunctions," Appl. Phys. Lett., 46:10, 970–972, May 15, 1985.

Klar et al., "Photomodulated reflectance study of $In_xGa_{1-x}$As/BaAs/AlAs microcavity vertical–cavity surface emitting laser structures in the weak–coupling regime: The cavity/ground–state–exciton resonance," Physical Review B, 59:4, 2894–2901, Jan. 15, 1999.

(Continued)

*Primary Examiner*—Hoa Q. Pham
(74) *Attorney, Agent, or Firm*—Vinson & Elkins L.L.P.

(57) ABSTRACT

A polarization modulation photoreflectance technique has been developed for optical characterization of semiconductor quantum confined structures. By using a tunable laser source in conjunction with polarization state modulation, a single beam modulation spectroscopy technique may be used to characterize the optical response of semiconductor materials and structures. Disclosed methods and instruments are suitable for characterization of optical signatures of quantum electronic confinement, including resolution of excitonic states at the band edge or other direct or indirect critical points in the band structure. This allows for characterization of semiconductor quantum well structures, for characterization of strain in semiconductor films, and for characterization of electric fields at semiconductor interfaces.

26 Claims, 6 Drawing Sheets

OTHER PUBLICATIONS

Miller et al., "Large room–temperature optical nonlinearity in GaAs/Ga$_{1-x}$Al$_x$as multiple quantum well structures," Appl. Phys. Lett., 41:8, 679–681, Oct. 15, 1982.

Pollak et al., "Room temperatureS, contactless electromodulation investigation of wafer–sized quantum well laser structure," SPIE 2693, 455–466, 1996.

Seraphin et al., "Franz–keldysh effect above the fundamental edge in germanium," Physical Review Letters, 14:5, 138–140, Feb. 1, 1965.

Shay, "Photoreflectance line shape at the fundamental edge in ultrapure GaAs," Physical Review B, 2:4, 803–807, Aug. 15, 1970.

Weiner et al., "Strong polarization–sensitive electroabsorption in GaAs/AlGaAs quantum well waveguides," Appl. Phys. Lett., 47:11, 1148–1150, Dec. 1, 1985.

Zheng et al., "Photoreflectance and the seraphin coefficients in quantum well structures," SPIE, 946, 43–47, 1988.

International Search Report issued on Mar. 10, 2005 for PCT/US04/15622.

* cited by examiner

POLARIZATION MODULATION PHOTOREFLECTANCE CHARACTERIZATION OF SEMICONDUCTOR QUANTUM CONFINED STRUCTURES

CROSS-REFERENCE TO RELATED APPLICATIONS

The present application claims benefit of U.S. Provisional Patent Application Ser. No. 60/472,687, filed on May 22, 2003.

FIELD OF THE INVENTION

The present invention relates to optical characterization of semiconductor quantum confined structures and, more particularly, to the use of polarization modulation photo-reflectance to characterize the physical properties of the quantum confined structure.

BACKGROUND OF THE INVENTION

High sensitivity optical measurement techniques are required in the fabrication of electronic and optoelectronic devices. The manufacture of semiconductor devices typically begins with a large substrate wafer of semiconductor material, and a large number of semiconductor devices are formed in each wafer. Because the device manufacturing steps are time consuming and expensive, it is important to the manufacturing process of such semiconductor devices that the physical characteristics of semiconductor device structures only vary within a small process window. In order to attain the earliest possible feedback during production, it is necessary to non-destructively characterize the physical properties of device structures before the device is complete. Importantly, the active region of many electronic and opto-electronic devices are semiconductor quantum confined structures. For example, the gain media in communications lasers typically comprise multiple quantum well structures. Unfortunately, widely available optical spectrometry techniques such as ellipsometry or linear reflectance do not have the sensitivity required to observe signatures of quantum confined structures. The signatures of quantum confinement occur in the vicinity of strong interband transition features such as the band gap, and typically have small amplitudes, in some cases as small as one part in $10^6$. Additional quantum confined optical signatures, arising from internal or interfacial electric fields also occur nearby to strong interband transition features. These signatures necessarily occur in the optical wavelength range, since semiconductor interband transitions occur in the ~1–5 eV range. Thus, high sensitivity optical techniques are needed in the extraction of semiconductor quantum confined signatures.

The requirement for high sensitivity may be met by a proven class of optical techniques known as modulation spectroscopy techniques. Modulation spectroscopy techniques such as "electro-reflectance" and "photo-reflectance" have exhibited sensitivity to differential changes in reflectivity as small as $10^{-7}$. Of the modulation spectroscopy techniques, photo-reflectance is best suited for use in the fabrication of electronic and optoelectronic devices, as it is nondestructive and only requires the sample have a reflecting surface (Aspnes, 1980). The conventional photo-reflectance configuration employs a diode laser pump beam to induce small periodic changes in electron-hole populations. Amplitude modulation of the pump beam is conventionally accomplished with an optical chopper, or by fixturing a polarizer at the output of a phase modulator. A second optical beam, coincident with the modulated pump beam is then used to monitor small sample reflectivity changes using phase locked detection. Thus, the conventional photo-reflectance configuration is a realization of electro-modulation, wherein the electric field is induced by the space charge separation field of the electrons and holes (Pollack, 1996). This dual pump-probe beam approach increases the system complexity.

Another problem with conventional photo-reflectometers is they lack a tunable pump beam with wavelengths nearby to at least one strong interband transition feature, or "critical point," in the band structure of the quantum confined structure. Importantly, quantum confinement shifts and sharpens spectral features near critical points in the optical absorption (Miller, 1982). Thus, by employing a tunable laser pump source with wavelength scanned across the critical point feature of interest in the band structure of the quantum confined structure, photo-reflectance information as a function of pump wavelength beam may be used to characterize the signatures of quantum confined structures.

Another problem with conventional photo-reflectometers is that they do not employ a polarization modulation technique to induce changes in the optical response of the quantum confined structure. By using polarization state modulation of the pump beam, and introducing the laser beam at a non-zero angle with respect to the surface normal, a component of polarization perpendicular to the sample surface is realized. Importantly, this polarization cannot be achieved by light incident normally onto the sample, as employed in conventional linear reflectance-difference spectroscopy (Aspnes, 1995). Generally, the optical response of a semiconductor quantum confined structure is anisotropic with respect to polarization vector. For example, when the quantum confined structure is a quantum well oriented parallel to the sample surface, light polarized in the plane of the quantum wells will couple to both "heavy-hole" and "light-hole" excitons, whereas light polarized normal to the plane of the well will couple preferentially to the "light-hole" excitons (Weiner, 1985). Thus, by introducing the polarization modulated laser beam at a non-zero angle with respect to the surface normal, anisotropy may be induced in the optical response of the quantum well. This feature of the polarization modulation technique is also useful for the characterization of strained layers, as strained layers are always quantum wells.

Thus, while conventional photo-reflectometers and optical spectrometers may be suitable for the particular purpose to which they address, they are not well suited for the characterization of the optical response of semiconductor quantum confined structures. The ability to record spectroscopic information using a single beam, which serves as both the pump and probe, greatly simplifies system operation. Moreover, although conventional photo-reflectometers may use a laser pump beam with sufficient power and focusing to create electric field modulation inside the sample, this pump is not wavelength tunable so as to characterize the signatures of quantum confined structures. Also, the laser pump is not polarization modulated so as to induce anisotropic optical responses associated with semiconductor quantum confined structures. Additionally, although conventional reflectance difference spectroscopy has been accomplished using polarization modulation, it has been implemented at normal incidence where no change in coupling to quantum confined states exists. Also, conventional reflectance difference spectroscopy uses lower laser powers.

In these respects, the polarization modulation photo-reflectometer according to the present disclosure substantially departs from the conventional concepts and designs of the prior art, and in so doing, provides an apparatus primarily developed for the characterization of optical signatures of quantum electronic confinement, including resolution of excitonic states at the band edge or other direct or indirect critical points in the band structure. This allows for characterization of quantum confinement, for characterization of strain in semiconductor films, and for characterization of electric fields at semiconductor interfaces.

SUMMARY OF THE INVENTION

In view of the foregoing disadvantages inherent in the known types of optical spectroscopy now present in the prior art, the present disclosure provides a new, single beam polarization modulation photo-reflectometer construction wherein the same can be utilized for the characterization of optical signatures of quantum electronic confinement, strain in semiconductor films, and for characterization of electric fields at semiconductor interfaces.

The general purpose of the present disclosure, which will be described subsequently in greater detail, is to provide a new polarization modulation photo-reflectometer that has many of the advantages of the optical spectroscopy mentioned heretofore and many novel features that result in a new polarization modulation photoreflectometer which is not anticipated, rendered obvious, suggested, or implied by any of the prior art, either alone or in any combination thereof.

The underlying principle of the polarization modulation photoreflectance technique is to characterize photoreflectance signals due to the optical response of quantum confined structures. Quantum confinement generally shifts and sharpens features in the optical response, and also enhances excitonic features without substantial broadening. Excitonic spectral widths are typically on the order of 8 meV, or approximately 5 nanometers in wavelength, at room temperature. Moreover, excitonic spectra associated with quantum confinement are anisotropic with respect to optical polarization. The polarization modulation photoreflectance technique provides the ability to generate and record photoreflectance information due to quantum confined optical response. To attain this, the present disclosure generally comprises a wavelength tunable diode laser, a laser controller and power supply, an electro-optic (EO) phase modulator with a function generator, an optical system, a sample, a photoreceiver, a signal conditioner, and a computer with measurement and system control software. The laser power is approximately 15 mW, with output wavelengths nearby to at least one critical point of the quantum confined semiconductor structure. The laser controller is controlled by the computer and performs power and wavelength scans. The polarization state modulator comprises an electro-optic (EO) phase modulator based on the Pockel's effect. The phase modulator is driven by an external function generator. The phase modulated laser beam is focused onto the sample and collected by the optical system. The different polarization state reflectivities produce an amplitude modulation of the laser intensity. The beam is directed to the photoreceiver which generates an electrical current proportional to the input intensity. The photoreceiver output comprises the AC signal at the modulation frequency and the DC photocurrent. The AC signal is divided by the DC signal, which provides normalization of the laser intensity. The AC signal is then proportional to the differential change in reflectivity. The signal conditioner then records the photoreceiver output. The computer controls the laser and records experimental photocurrents from the signal conditioner. Thus photoreflectance wavelength information related to the optical response of quantum confined structures is acquired.

The semiconductor materials that are the subject of the present disclosure may be any semiconductor materials containing quantum confined structures, and may include, but are not limited to Group III–V semiconductor materials or Group II–IV semiconductor materials. In certain embodiments such materials may include gallium arsenide, gallium aluminum arsenide, gallium nitride, aluminum nitride, gallium phosphide, indium gallium arsenide, indium antimonide, or combinations thereof, or they may include silicon, germanium, silicon germanium, carbon, silicon carbide, zinc oxide, zinc sulfide, cadmium sulfide, cadmium selenide, or combinations thereof.

There has thus been outlined, rather broadly, the more important features of the disclosure in order that the detailed description thereof may be better understood, and in order that the present contribution to the art may be better appreciated. There are additional features of the disclosure that will be described hereinafter.

In this respect, before explaining at least one embodiment of the disclosure in detail, it is to be understood that the disclosure is not limited in its application to the details of construction and to the arrangements of the components set forth in the following description or illustrated in the drawings. The disclosure is capable of other embodiments and of being practiced and carried out in various ways. Also, it is to be understood that the phraseology and terminology employed herein are for the purpose of the description and should not be regarded as limiting. This disclosure may be embodied in the form illustrated in the accompanying drawings, attention being called to the fact, however, that the drawings are illustrative only, and that changes may be made in the specific construction illustrated.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

The following discusses use of the inventive polarization modulation photoreflectance (PMPR) technique for characterization of quantum well structures. It is understood that the PMPR technique of the present drawings may be used to analyze any quantum confined structure, the discussion of quantum well structures considered to be exemplary only and in no way limiting in scope.

Figure 1:
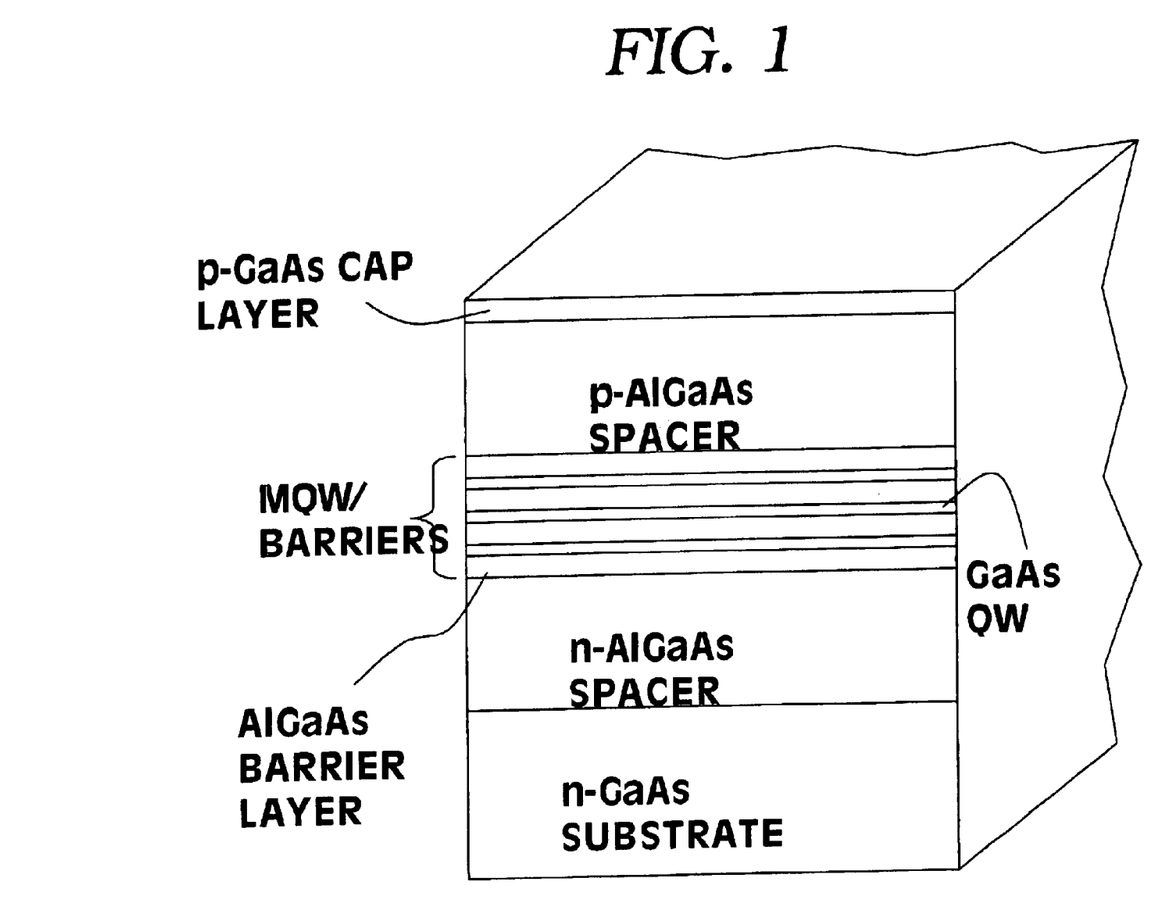
FIG. 1 illustrates an exemplary quantum well test structure that may be analyzed using the photo-reflectance technique of the present disclosure.

Turning now descriptively to the drawings, in which similar reference characters denote similar elements throughout the several views, FIG. 1 contains, in an exaggerated view, an exemplary quantum well test structure that may be characterized using the polarization modulation photo-reflectance technique of the present disclosure. Quantum well test structure, which may be grown using molecular beam epitaxy, comprises a negatively doped gallium arsenide (GaAs) semiconductor substrate upon which is grown an negatively doped aluminum gallium arsenide (AlGaAs) "spacer" layer of ~94.5 nanometer thickness. An undoped barrier layer comprising AlGaAs is grown on the spacer layer. Then a multiple quantum well section comprising a number of periods of GaAs quantum wells and AlGaAs barrier layers is grown on the first barrier layer. In an exemplary embodiment, individual quantum wells may comprise a thickness of approximately 7.4 nanometers, and barriers may comprise a thickness of approximately 7.4 nanometers. A second confinement layer is grown on the multiple quantum well section. Quantum well test structure further comprises an additional AlGaAs spacer layer of approximately 94.5 nanometer thickness, followed by a thin GaAs capping layer.

Figure 2:
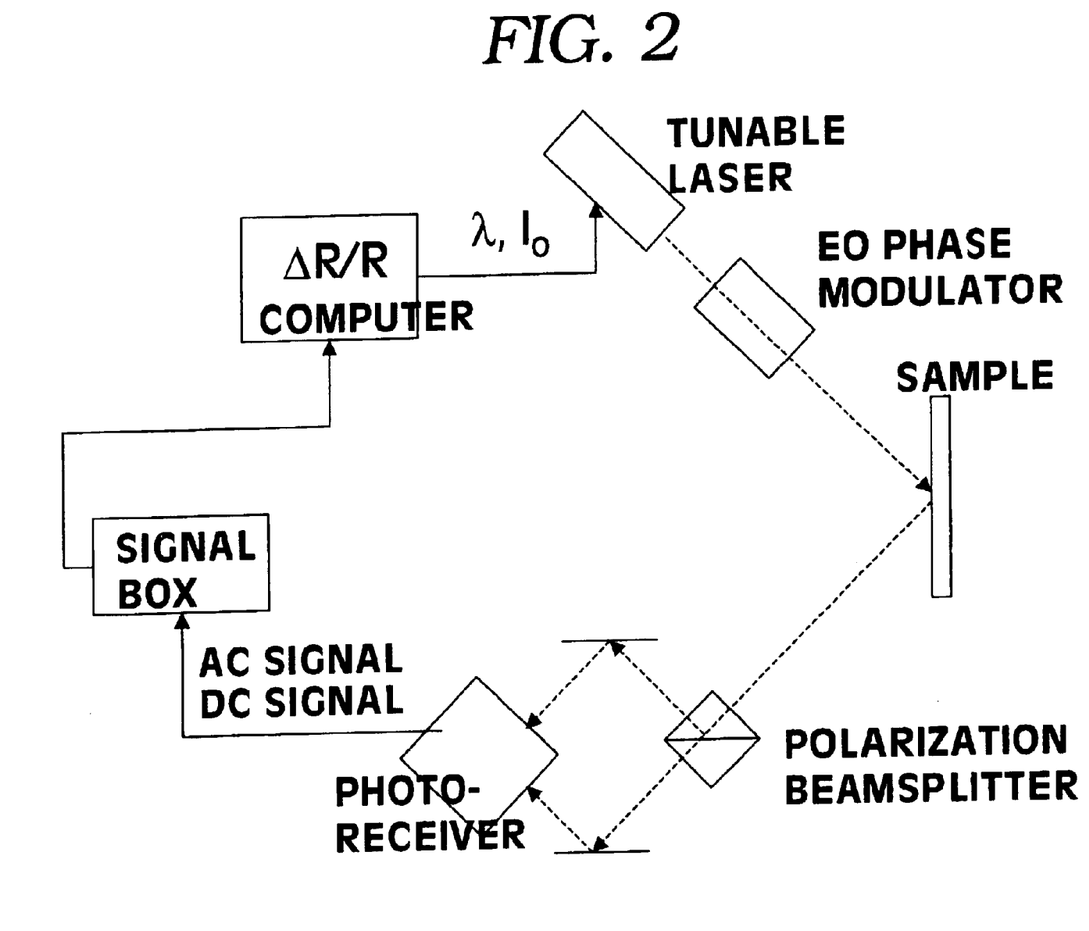
FIG. 2 contains an arrangement of the polarization modulation photo-reflectivity apparatus which may be used to provide the polarization modulation photo-reflectance characterization in accordance with present disclosure.

In accordance with the arrangement of the present disclosure as shown in FIG. 2, polarization modulation photo-reflectance may be used to measure the reflected spectra from quantum well test structure, or any other quantum confined device structure, in order to characterize the properties the quantum confined structure, and importantly, establish the energy of optical transitions in quantum confined structure, establish the form of the dielectric function in the vicinity of said optical transitions, and profile the excitonic states in the vicinity of said optical transitions. Quantum confinement is known to enhance excitonic features, often making them visible at room temperature (Miller, 1982). By introducing the laser beam at a non-zero angle of incidence with respect to the quantum well layers, a component of polarization perpendicular to the plane of the quantum well layers is realized. This polarization cannot be achieved by light incident normally onto the sample, and shows different selection rules. In particular, for polarization components perpendicular to the quantum well layers, the "heavy-hole" excitonic absorption strength is transferred to the nearby "light-hole" absorption (Weiner, 1985). As shown in FIG. 2, polarization modulation photo-reflectance arrangement comprises a tunable diode laser, a laser controller, an electro-optic (EO) phase modulator with a function generator, an optical system, a sample, a photoreceiver, a signal conditioner, and a computer with measurement and system control software.

Figure 3:
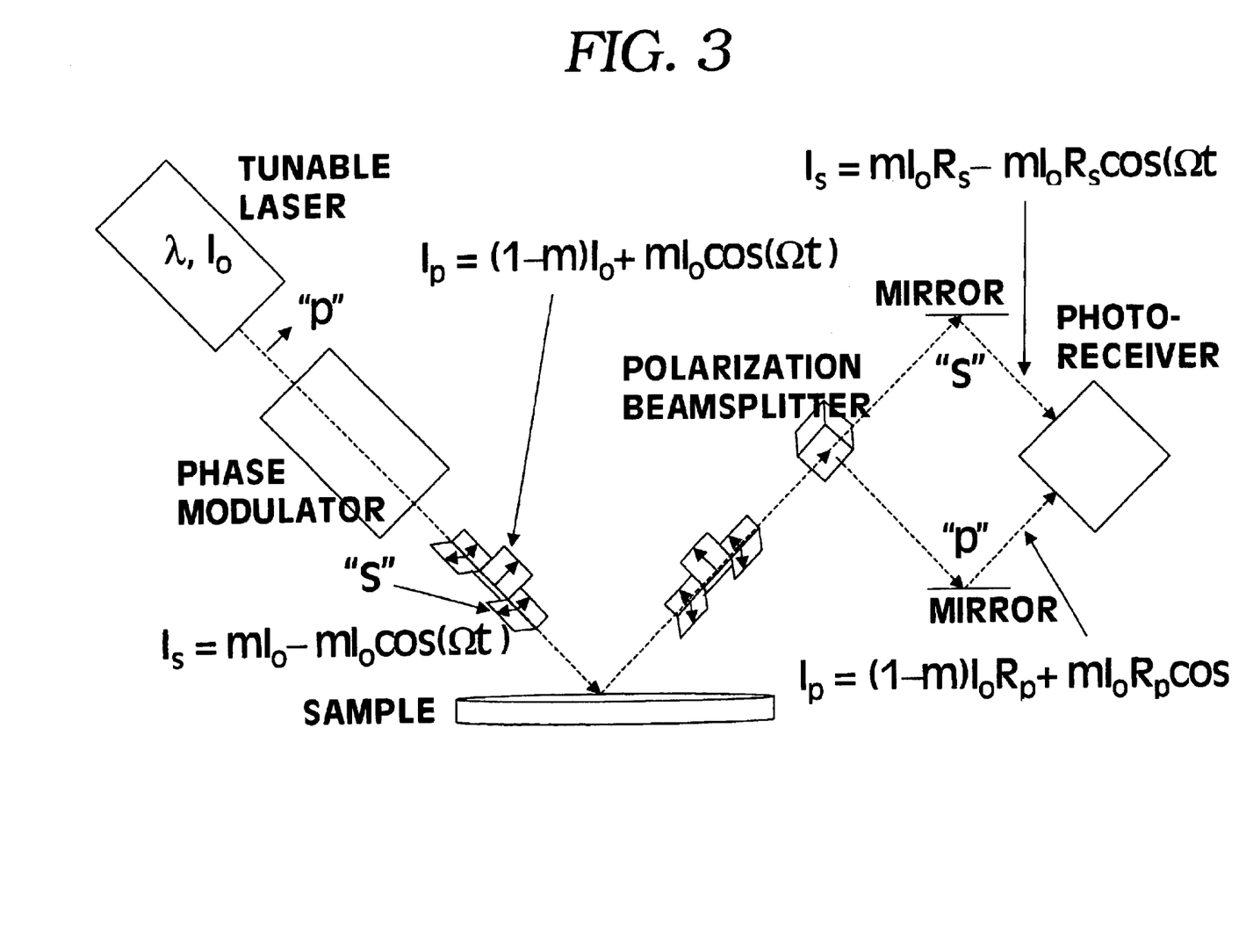
FIG. 3 is a schematic representation of the polarization state through the optical system.

The laser diode is an external cavity tunable laser diode with center wavelength of approximately 844 nm and tunable range of approximately 20 nanometers. Laser embodiments include external cavity tunable diode lasers emitting in the UV-NIR wavelength range (200–1700 nm). The laser power is approximately 15 mW. However, laser embodiments include lasers operating at powers of approximately 5 mW or above. The laser controller is a programmable power source compatible with the laser diode and may be controlled by the computer. The laser beam is directed into the electro-optic (EO) phase modulator where its polarization state is modulated. In an exemplary embodiment phase modulator has a resonant frequency of approximately 20 MHz and is driven sinusoidally by an external function generator. The phase modulator will typically operate at or above 1 MHz and may be driven by an external function generator. Embodiments also include broadband phase modulation, including DC bias operation. Once the laser beam exits from the phase modulator, it may have a small "residual amplitude modulation" induced by the phase modulator. The phase modulator design minimizes residual amplitude modulation. However, any residual amplitude modulation produces a constant or sloping background which may be removed. The polarization modulated laser beam is then focused onto the sample surface at an angle of incidence of approximately 45°. The optical system comprises various optical elements including focusing and collimation lenses, and mirrors. All optical elements are matched to the laser source wavelength. Once the laser beam is reflected from the sample surface, it has sources of amplitude modulation at the modulation frequency from the difference in reflectivity due to the polarization state change, including any polarization induced anisotropy in the semiconductor optical response, and any residual amplitude modulation. The reflected beam is collected and focused onto the photodiode. FIG. 3 shows the polarization state of the laser beam as it passes through the optical system.

As an exemplary mode of operation, the unmodulated laser beam is directed onto the sample with polarization parallel to the plane of incidence, also known as "p" polarization. The phase modulator then places a portion of the incident intensity into the polarization perpendicular to the plane of incidence, also known as "s" polarization, at the modulation frequency. The intensity of the "p" polarized light may be written:

$$I_p = I_o(1-m)R_p + mI_oR_p \cos(\Omega t),$$

while the intensity of the "s" polarized channel is:

$$I_s = mI_oR_s - mI_oR_s \cos(\Omega t),$$

where $R_s$ and $R_p$ are the reflectivities of the "s" and "p" polarized light, respectively, m is the amplitude of the sinusoidal intensity modulation of either polarization channel, and $\Omega$ is the modulation frequency. The laser beam contains the sum of these intensities which may be written:

$$I_p + I_s = I_oR_p - mI_o(R_p - R_s) + mI_o(R_p - R_s)\cos(\Omega t).$$

This is of the form $I_o[R - \Delta R + \Delta R \cos(\Omega t)]$, where $\Delta R \equiv m(R_s - R_p)$. Also, the respective intensities may be split onto separate beams by the use of a polarizing beamsplitting cube, and the laser beams containing either polarization state then directed into a photoreceiver comprising two photodiodes connected through a subtraction circuit. The photoreceiver output then contains an electrical current proportional to the difference in these intensities, which may be written:

$$I_p - I_s = I_oR_p - mI_o(R_p + R_s) + mI_o(R_p + R_p)\cos(\Omega t).$$

This is again of the form $I_o[R - \Delta R + \Delta R \cos(\Omega t)]$, where $\Delta R$ is now $\Delta R \equiv m(R_s + R_p)$.

Figure 4:
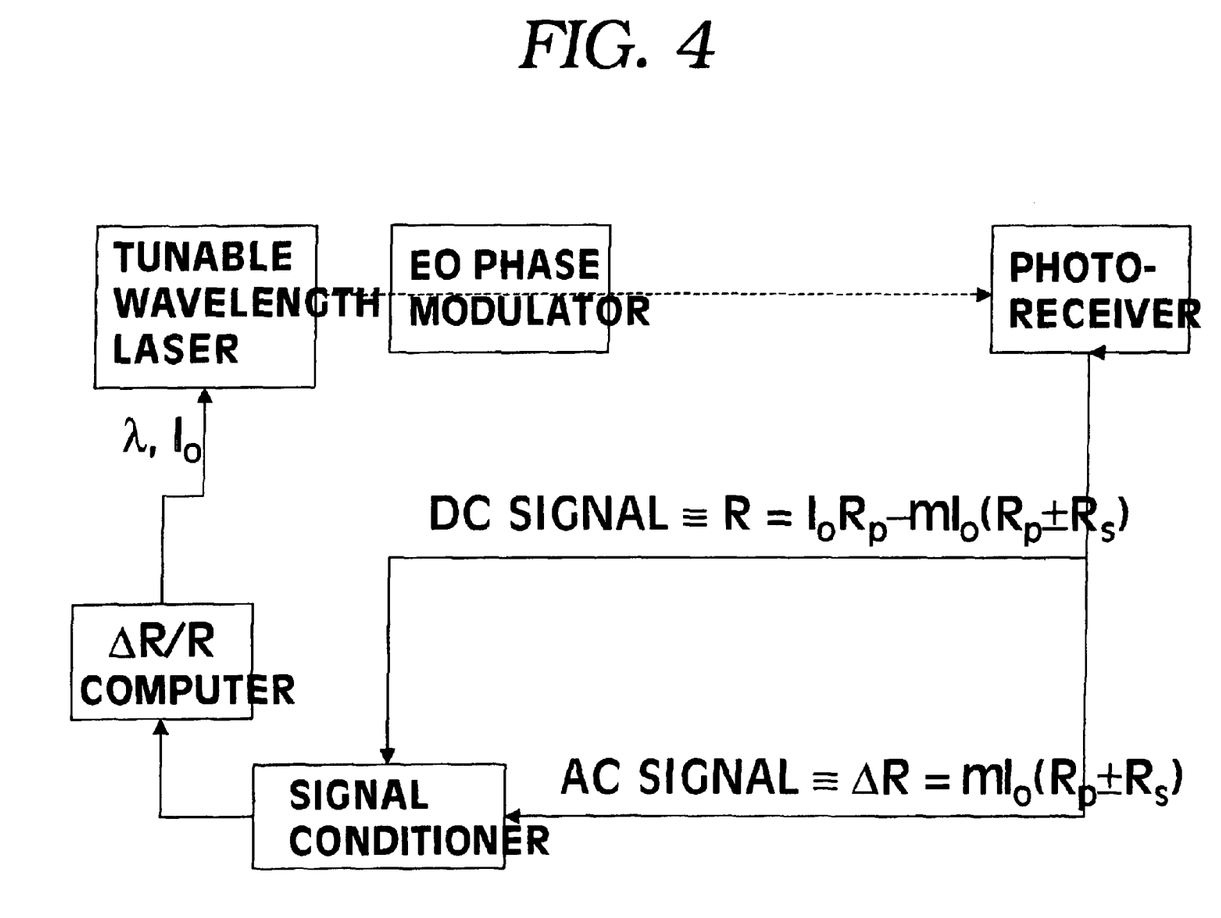
FIG. 4 is block diagram of the electronic signals of the polarization modulation photo-reflectance apparatus.

FIG. 4 contains the block diagram of the electrical signals in the polarization modulation apparatus. The DC signal from the photoreceiver is proportional to $I_o[R - \Delta R]$, while the AC signal is proportional to $I_o \Delta R$. In order to measure $\Delta R/R$, the laser intensity $I_o$ must be eliminated. This is accomplished by dividing the AC signal by the DC photocurrent. This normalized AC signal is proportional to $\Delta R/R + O(\Delta R/R)^2$.

In an exemplary case where the polarization modulation is small, $R \equiv R_p$, then $\Delta R/R$ may be written $\Delta R/R \equiv m(R_s/R_p +$ 1). Now, letting $R_s \to R_s + \Delta R_s$, and $R_p \to R_p + \Delta R_p$, where $\Delta R_s$ and $\Delta R_p$ now refer to the induced changes in semiconductor optical response for the "s" and "p" polarization, respectively, $\Delta R/R$ becomes $$\Delta R/R \cong m(R_s/R_p + 1) + mR_s/R_p(\Delta R_s/R_s + \Delta R_p/R_p).$$

The first term is proportional to the sum of the linear "s" and "p" channel reflectivities. The information contained in this term is equivalent to the information contained in conventional ellipsometric data and may be used to determine filmstack parameters such as film thickness. Typically, over the wavelength interval of tunable laser, this first term produces a slowly varying background, of magnitude on the order of $10^{-1}$. This term may be eliminated from $\Delta R/R$, revealing the second, derivative-like term, which is due to the induced due changes in semiconductor optical response. These are the well-known photo-reflectance spectra (Aspnes, 1980; Shay, 1970). Typical values of the photo-reflectance signal from semiconductor quantum confined structures range in amplitude from $\sim 10^{-2} - 10^{-5}$ (Pollack, 1994), with spectral widths typically $\leq 10$ meV at room temperature (Weiner 1985; Shay 1970). The signal conditioner records the photoreceiver output. The computer controls the laser wavelength and intensity and records the measurement photocurrents. Thus $\Delta R/R$ is recorded as a function of laser wavelength and intensity. Embodiments include alterations to the arrangement which do not alter the fundamental polarization modulation photo-reflectance signal. Embodiments also include any configurations where the photoreceiver AC signal contains a photo-reflectance signal due changes in sample semiconductor optical response induced by the change in pump beam polarization state. As used herein, the photoreflectance signal is photo-induced changes in the semiconductor optical response, and the linear reflectance signal is the difference in the linear reflectivity of the "s" and "p" components of polarization.

Figure 5:
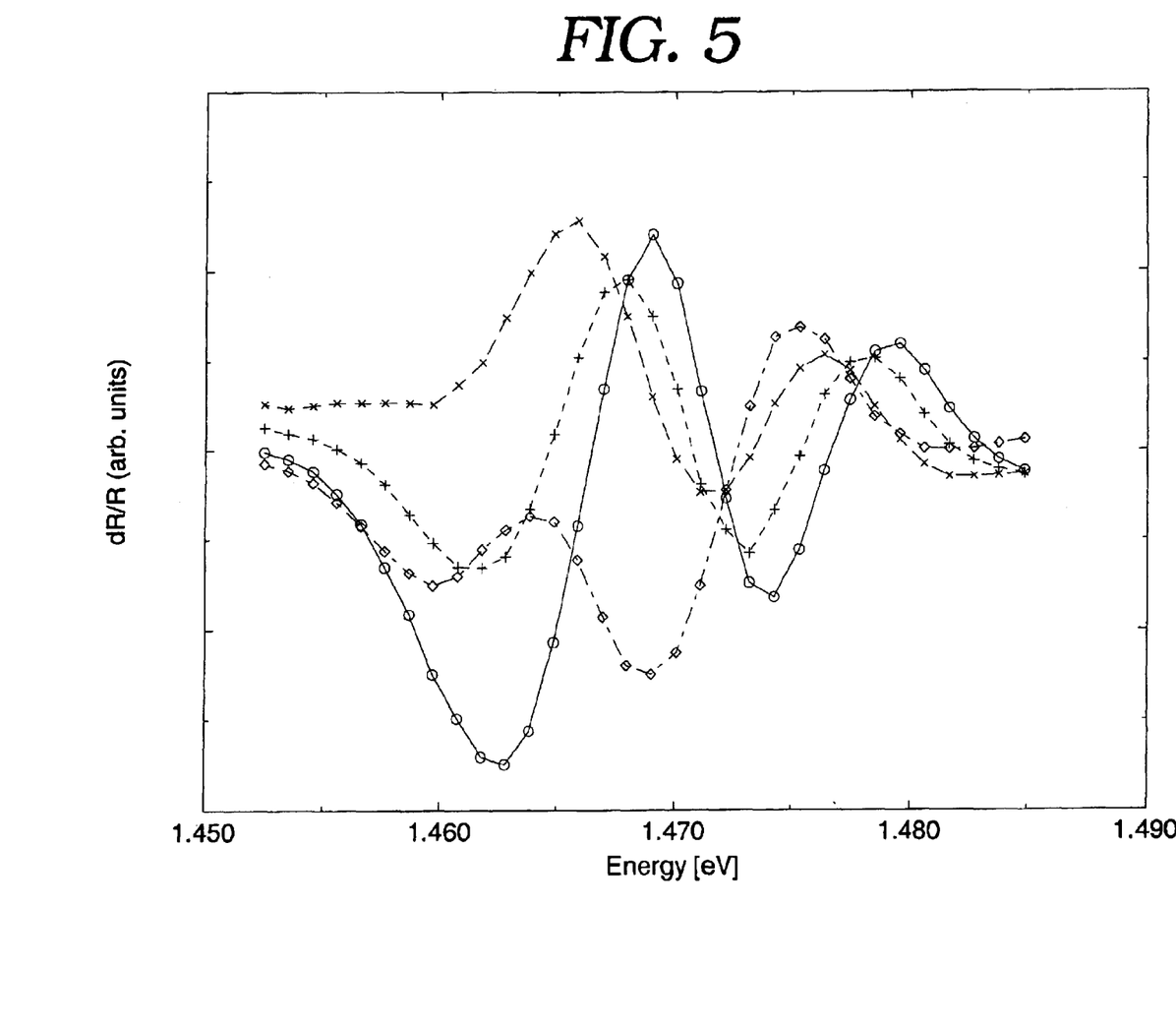
FIG. 5 is a graph of the polarization modulation photo-reflectance spectrum obtained from quantum well test structure.
Figure 6:
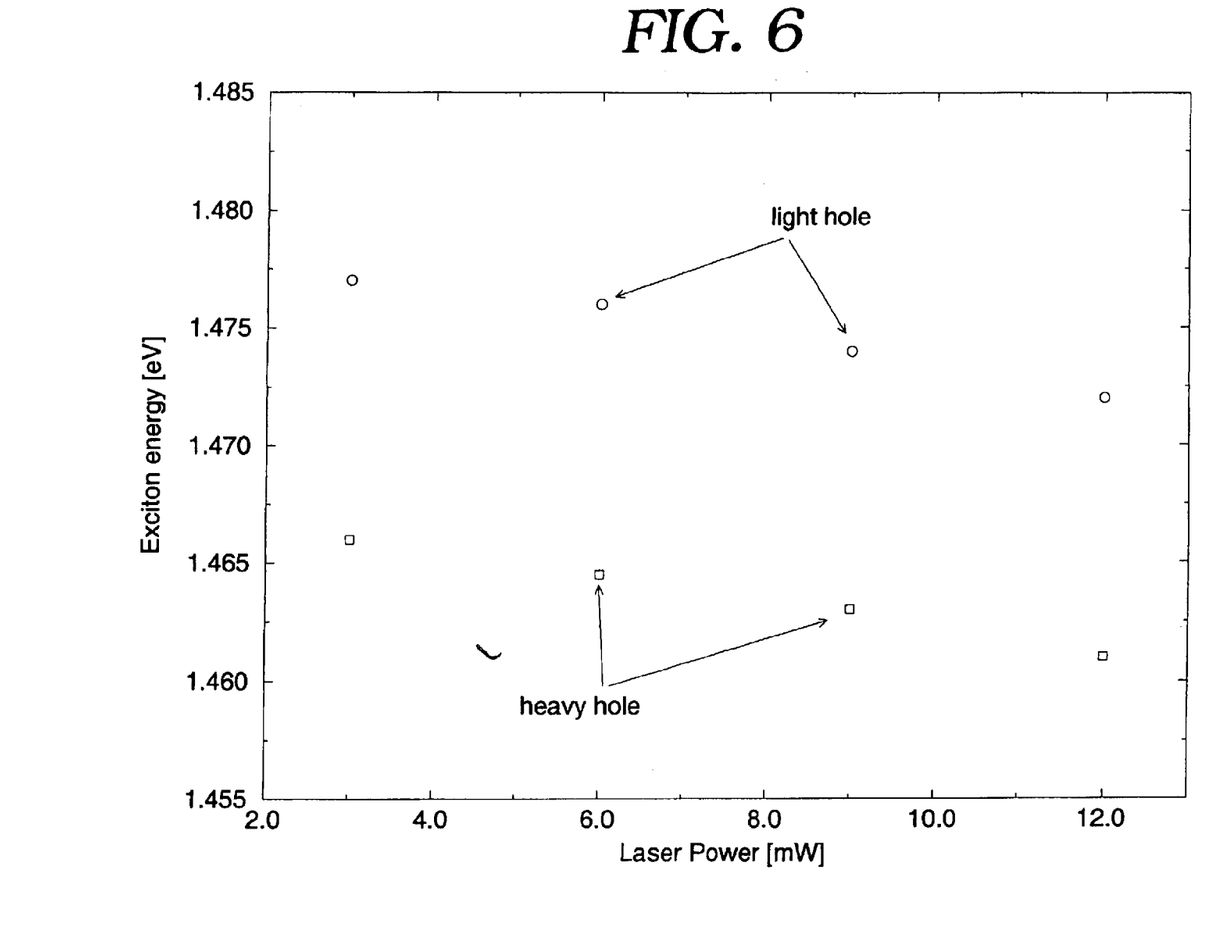
FIG. 6 shows shifting of quantum well excitonic positions as laser intensity is increased.

The underlying principle of the polarization modulation photo-reflectivity technique is to characterize the photo-reflectance spectra associated with semiconductor quantum confined structures, and to derive critical point parameters associated with quantum confined structures such as excitonic resonance energies and spectral widths. Critical point parameters generally characterize the "active" electronic properties of quantum confined structures. Excitonic features are enhanced in the presence of quantum confinement and characterize the splitting of the "light-hole" and "heavy-hole" excitons associated with quantum confinement or strain. As is well known, the photoreflectance spectrum is proportional to the derivative of the dielectric function. The dielectric function of critical point and excitonic resonance features may be written:

$$\epsilon(E, \Gamma) = A \exp\{i\phi\}/(E - E_g + i\Gamma)^n,$$

where E is the photon energy, A is the oscillator amplitude, $\phi$ is the phase projection, Eg is the oscillator energy, $\Gamma$ is the broadening, and n is an exponent which characterizes the dimensionality of the resonance (Aspnes, 1980). Due to the dependence of excitonic optical response on input polarization, amplitude analysis may be used to quantify anisotropies in the polarization modulation photo-reflectivity technique. However, the oscillator energy, Eg, and the spectral width, $\Gamma$, are the primary parameters of interest. Excitonic resonances are typically 4–6 meV in spectral width, and often remain unbroadened at room temperature. Both Eg and $\Gamma$ may be determined simply from the lineshape of $\Delta R/R$ itself (Aspnes, 1980). The amplitude, broadening, and position of excitonic absorptions are strongly influenced by internal fields generated by photo-excited carriers. FIG. 5. illustrates photo-reflectance data from quantum well test structure exposed to a series of polarization modulation photoreflectivity wavelength scans at laser powers of 3 mW, 6 mW, 9 mW, and 12 mW. The linear reflectance background has been removed using a polynomial fit. The data is scaled with increasing laser power and curves are included to guide the eye. In these scans, the PMPR spectra shows derivative structure at "heavy-hole" and "light-hole" excitonic positions. This feature of polarization modulation photoreflectivity also makes it ideal for the characterization of strain, since the major effect of uniaxial stress is to shift and split the excitonic features. Each curve is analyzed using the lineshape of $\Delta R/R$ (Aspnes, 1980), which reveals a redshift of the excitonic energy Eg as laser intensity is increased. Excitonic positions derived from this data are shown in FIG. 6. The excitonic widths are essentially independent of laser intensity. The total redshift for either the light hole or the heavy hole is approximately 5 meV. For quantum well test structure, excitonic redshifts of approximately 1 meV per 6 kV/cm internal electric field are expected. This shift is due to space-charge separation of photo-excited carriers. Thus, the observed shifts are indicative of internal electric fields approximately 30 kV/cm in magnitude. Such fields can also be directly measured by photo-reflectance using the above bandgap Franz-Keldysh oscillations (Gray, 2001; Seraphin, 1965). However, the polarization modulation photoreflectivity technique provides a means to determine interfacial electric fields from line-shape analysis.

Thus, this disclosure is suitable for the characterization of the polarization modulated photo-reflectance as a function of laser intensity and laser wavelength. A tunable diode laser provides the optical intensity needed to induce changes in the optical response of semiconductor quantum confined structures due to space-charge separation of electrons and holes. The laser controller provides intensity and wavelength control for the tunable laser diode. The computer may program laser scans via interface to the laser controller. The EO phase modulator modulates the polarization state of the laser beam at approximately 20 MHz. An external function generator is used to provide drive current to the electro-optic modulator. The phase modulated laser beam is then focused onto the semiconductor sample structure. Reflected light is collected and directed onto a photoreceiver. The photoreceiver provides, as output, an AC signal proportional to the sum or difference of sample "s" and "p" reflectivities. The photoreceiver AC signal is normalized by the DC photocurrent. The AC signal is provided to the signal conditioner, which performs bandwidth limited detection at the EO modulation frequency. The conditioned signal is then passed to the computer, which stores $\Delta R/R$ as a function of laser parameters. The linear reflectivity contribution to the AC signal is removed by a fit to the slowly varying linear reflectivity background. Thus, the polarization modulated photo-reflectance arrangement characterizes the polarization modulated photo-reflectance signal as a function of laser intensity and laser wavelength.

As to a further discussion of the manner of usage and operation of the present disclosure, the same should be apparent from the above description. Accordingly, no further discussion relating to the manner of usage and operation will be provided.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

REFERENCES

U.S. Patent Documents:

| | | | |
|---|---|---|---|
| 6,195,166 | February 2001 | Gray | 356/477 |
| 4,931,132 | June 1990 | Aspnes | 156/601 |
| 3,982,207 | March 1975 | Dingle | 331/94.5 |

Other Publications:

"Photomodulated reflectance study of InGaAs/GaAs/AlAs microcavity vertical-cavity surface emitting laser structures in the weak-coupling regime: The cavity/ground-state-exciton resonance," P. J. Klar et al., Phys. Rev. B 59, 2894 (1999).

"Room Temperature, Contactless Electromodulation Investigation of Wafer-Sized Quantum Well Laser Structures," F. H. Pollack et al., SPIE vol. 2693, pp. 455–466 (1996).

"Observation and analysis of epitaxial growth with reflectance-difference spectroscopy," D. E. Aspnes, Mater. Sci. Eng. B30, 109–119 (1995).

"Modulation Spectroscopy of Semiconductors and Semiconductor Microstructures," F. H. Pollack, in *Handbook on Semiconductors*, Vol. 2, edited by M. Balkanski, pp. 527–635 (North-Holland, Amsterdam, 1994).

"Photoreflectance study of photovoltage effects in GaAs diode structures," V. M. Airaksinen and H. K. Lipsanen, Appl. Phys. Lett. 60, 2110 (1992).

"Photoreflectance and the Seraphin coefficients in quantum well structures," X. L. Zeng et al., SPIE vol. 946, pp. 43–47 (1988).

"Photoreflectance characterization of interband transitions in GaAs/AlGaAs multiple quantum wells and modulation-doped heterojunctions," O. J. Glembocki et al., Appl. Phys. Lett. 46, 970–972 (1985).

"Strong polarization-sensitive electroabsorption in GaAs/GaAlAs quantum well waveguides," J. S. Weiner et al., Appl. Phys. Lett. 47, 1148–1150 (1985).

"Large room-temperature nonlinearity in GaAs/Ga(1-x)AlxAs multiple quantum well structures," D. A. B. Miller et al., Appl. Phys. Lett. 41, 679–681 (1982).

"Modulation Spectroscopy," D. Aspnes, in *Handbook on Semiconductors*, Vol. 2, edited by M. Balkanski, pp. 109 (North-Holland, Amsterdam, 1980).

"Photoreflectance Line Shape at the Fundamental Edge in Ultrapure GaAs," J. L. Shay, Phys. Rev. B 2, 803–807 (1970).

"Franz-Keldysh Effect Above the Fundamental Edge in Germanium," B. O. Seraphin and R. B. Hess, Phys. Rev. Lett. 14, 138–140 (1965).

What is claimed is:

1. A method of determining physical characteristics of a semiconductor quantum confined structure, the method comprising the steps of:

a) illuminating an area of a surface of a semiconductor material wherein the semiconductor material comprises one or more quantum confined structures with a wavelength tunable laser beam having a center wavelength nearby to at least one "critical point" in the optical response of a semiconductor quantum confined structure, with a wavelength tuning range of approximately 15 nm or greater, and using a focal spot size of 40 microns or less, wherein the laser beam is passed through an electro-optic phase modulator operating at or above 1 MHz frequency to achieve modulation of the polarization state of tunable laser beam prior to illuminating the quantum confined structure;

b) recording the reflected alternating current light from the illumination of the quantum confined structure, wherein the alternating current light contains one of the photo-induced changes in the semiconductor optical response, known as the photoreflectance signal, and the difference in the linear reflectivity of the "s" and "p" components of polarization, known as the linear reflectance signal or both;

c) repeating steps a) and b) across the tuning range of the laser source of step so as to collect wavelength information in the vicinity of critical points in the optical response of the semiconductor quantum confined structure;

d) repeating steps a) and b) across the power range of the laser source so as to collect intensity information in the vicinity of critical points in the optical response of the semiconductor quantum confined structure; and e) using the information collected in steps c) and/or d) to detect physical characteristics of the quantum confined structure.

2. The method as defined in claim 1, wherein the quantum confined structures comprise semiconductor quantum wells, semiconductor quantum wires, semiconductor quantum dots, or interfacial layers.

3. The method as defined in claim 1 wherein wavelength information is recorded related to a quantum confined structure and the linear reflectance spectrum is removed from the polarization modulation photoreflectance data using a fit to the linear reflectance background.

4. The method as defined in claim 1 wherein wavelength information is recorded related to critical points associated with quantum confined structures, and is used to derive critical point position, shape, amplitude, spectral width, and/or phase parameter.

5. The method as defined in claim 4 wherein a value of internal electric field is derived.

6. The method as defined in claim 4 wherein changes in critical point parameters as a function of laser intensity are determined.

7. The method as defined in claim 6, wherein changes in critical parameters as a function of laser intensity are used to predict the behavior of a quantum confined structure under device operational conditions, before the final device is complete.

8. The method as defined in claim 6 wherein changes in interfacial charge density or interfacial electric fields are correlated to changes in critical point parameters.

9. The method as defined in claim 1 wherein wavelength information is recorded related to excitonic features associated with quantum confined structures, and the excitonic positions and splitting are derived.

10. The method as defined in claim 9 wherein performing a value of strain is derived.

11. The method as defined in claim 1 wherein wavelength information is recorded related to excitonic features associated with quantum confined structures, and the excitonic amplitudes are derived.

12. The method as defined in claim 1, wherein the laser beam illuminates the semiconductor material at an angle of incidence of about 45°.

13. The method as defined in claim 1, wherein the polarization modulated light comprises a component of polarization perpendicular to the surface of the semiconductor material and a component of polarization parallel to the surface of the semiconductor material.

14. The method as defined in claim 1, wherein the data is used to extract information related to the photo-reflectance spectrum of the quantum confined structure, the photo-reflectance spectrum consisting of the polarization modulation anisotropic response of the quantum confined structure.

15. The method as defined in claim 1, wherein the reflected beam is passed through a polarization beam splitter prior to being recorded.

16. The method as defined in claim 1, wherein the semiconductor material comprises a group III–V semiconductor material.

17. The method as defined in claim 1, wherein the semiconductor material comprises gallium arsenide, gallium aluminum arsenide, gallium nitride, aluminum nitride, gallium phosphide, indium gallium arsenide, indium antimonide, or combinations thereof.

18. Apparatus for detecting physical characteristic of a semiconductor quantum confined structure, comprising:
    a wavelength tunable diode laser;
    a laser controller effective to perform power and wavelength scans;
    a power supply connectable to supply power to the laser;
    a polarization state modulator effective to produce phase modulation of a light beam from the laser;
    an optical system effective to direct light reflected from a sample into a photoreceiver;
    a photoreceiver configured to generate an electrical current proportional to the input intensity;
    a signal conditioner connected to record the photoreceiver output; and
    a computer with measurement and system control software.

19. The apparatus of claim 18, wherein the laser power is approximately 15 mW with output wavelengths nearby to at least one critical point of a quantum confined semiconductor structure.

20. The apparatus of claim 18, wherein the polarization state modulator comprises an electro-optic (EO) phase modulator based on the Pockel's effect driven by an external function generator.

21. The apparatus of claim 18, wherein the optical system comprises a polarization beam splitter.

22. The apparatus of claim 18, further comprising a semiconductor material comprising one or more quantum confined structures.

23. The apparatus of claim 22, wherein the semiconductor material comprises a vertical cavity surface emitting laser.

24. The apparatus of claim 22, wherein the semiconductor material is a Group II–IV semiconductor material.

25. The apparatus of claim 22, wherein the semiconductor material comprises silicon, germanium, silicon germanium, carbon, silicon carbide, zinc oxide, zinc sulfide, cadmium sulfide, cadmium selenide, or combinations thereof.

26. The apparatus of claim 22, wherein the semiconductor material comprises a wafer.

* * * * *